United States Patent

Breitenbach et al.

[11] Patent Number: 5,945,032
[45] Date of Patent: Aug. 31, 1999

[54] POLYMER/HYDROGEN PEROXIDE COMPLEXES

[75] Inventors: Jörg Breitenbach, Mannheim; Bernhard Fussnegger, Kirrweiler; Siegfried Lang, Ludwigshafen; Hans-Bernd Reich, Neuhofen, all of Germany

[73] Assignee: BASF Aktiengesellschaft, Ludwigshafen, Germany

[21] Appl. No.: 08/935,656

[22] Filed: Sep. 23, 1997

[30] Foreign Application Priority Data

Sep. 30, 1996 [DE] Germany .......................... 196 40 365

[51] Int. Cl.⁶ .................... C01B 15/037; A01N 25/26; A61K 33/40
[52] U.S. Cl. .................... 252/186.29; 424/53; 424/62; 424/78.24; 424/78.25; 424/419; 424/616; 510/116; 510/311; 514/859; 516/101
[58] Field of Search .......................... 252/186.28, 315.2, 252/186.29; 510/311, 116; 424/62, 616, 78.25, 78.24, 53, 419; 514/859

[56] References Cited

U.S. PATENT DOCUMENTS

| | | |
|---|---|---|
| 2,105,835 | 1/1938 | Krause .......................... 252/186.28 X |
| 3,082,193 | 3/1963 | Mendelsohn .................... 424/78.24 X |
| 3,350,265 | 10/1967 | Rubinstein et al. ................ 424/616 X |
| 3,376,110 | 4/1968 | Shiraeff ........................ 252/186.28 X |
| 4,020,005 | 4/1977 | Lang .............................. 252/315.1 X |
| 4,027,008 | 5/1977 | Sokol ............................ 252/186.28 X |
| 4,320,114 | 3/1982 | Denzinger .......................... 424/80 |
| 4,646,730 | 3/1987 | Schonfeld et al. .................... 728/156 |
| 4,915,955 | 4/1990 | Gömöri .............................. 424/616 |
| 5,008,106 | 4/1991 | Merianos et al. .................. 424/616 X |
| 5,159,033 | 10/1992 | Merianos et al. ...................... 526/201 |
| 5,190,749 | 3/1993 | Login et al. ...................... 424/616 X |
| 5,364,601 | 11/1994 | Salpekar ................................ 422/28 |
| 5,409,697 | 4/1995 | Gluck .................................... 424/78 |
| 5,437,858 | 8/1995 | Hungerbach et al. ............. 424/616 X |
| 5,716,634 | 2/1998 | Tseng et al. ........................ 424/62 X |

FOREIGN PATENT DOCUMENTS

| | | |
|---|---|---|
| 107376 | 5/1984 | European Pat. Off. . |
| 334 176 | 9/1989 | European Pat. Off. . |

*Primary Examiner*—Richard D. Lovering
*Attorney, Agent, or Firm*—Keil & Weinkauf

[57] ABSTRACT

Polymer complexes which comprises hydrogen peroxide, a polymer suitable for complex formation with hydrogen peroxide, and at least one metal colloid and/or metal salt are prepared as described and used in bactericidal compositions, disinfectant systems, hair cosmetic compositions and as free-radical initiators for chemical reactions.

12 Claims, No Drawings

POLYMER/HYDROGEN PEROXIDE COMPLEXES

The present invention relates to polymer complexes which comprise hydrogen peroxide, a polymer suitable for complex formation with hydrogen peroxide, and at least one metal colloid and/or metal salt.

Hydrogen peroxide has many commercial and industrial applications as oxidizing agent and bleach, disinfectant, deodorizing agent, and as radical initiator for chemical processes, for example for polymerizations (see Römpp Chemie-Lexikon, 9. Edition "Wasser-stoffperoxid" and literature cited therein). It is becoming increasingly important in particular as disinfectant because it is more environmentally compatible than halogenated disinfectants.

However, hydrogen peroxide undergoes noticeable decomposition on exposure to heat or light or in the presence of impurities such as dust, various metal salts and alkaline substances. Although the decomposition is desired for most applications, the shelf life and useability are limited because the hydrogen peroxide content decreases.

Besides stabilization by classical stabilizers such as silicates, phosphates, gelatin, dextrines and complexing agents, the stabilization of hydrogen peroxide by colloidal solutions of metals, in particular by silver colloids, has been described (DE-A 3 620 609, EP-B 596 908).

Hydrogen peroxide can also be stabilized in the form of complexes with polymers, preferably polyvinylpyrrolidones. Complexes of this type are described, for example, in U.S. Pat. No. 3,376,110, U.S. Pat. No. 3,480,557, U.S. Pat. No. 5,077,047, U.S. Pat. No. 5,108,742, WO-A 91/07184 and WO-A 92/17158. These complexes are, as a rule, stable powders which are easy to handle and can be incorporated into a large number of formulations. The rate at which hydrogen peroxide is released to the surrounding medium depends on the strength of the binding of the hydrogen peroxide to the polymeric carrier. The rate at which the hydrogen peroxide displays its chemical effect depends, by contrast, on the decomposition catalysts present in the medium (dust particles, basic impurities, traces of metals).

It is furthermore known that polyvinylpyrrolidone can be employed as protective polymer for metal colloid solutions, for example of copper, silver (Hirai et al., Makromol. Chem. Rapid Commun. 5 (1984) 381), palladium, gold, rhodium or platinum. Esumi et al. described the preparation of colloidal silver solutions in the presence of vinyl alcohol and N-vinylpyrrolidone (J. Appl. Polym. Sci. 44 (1992) 1003) or polyvinylpyrrolidone homopolymers (Hirai et al. J. Macromol. Sci. Chem. A13 (1979) 633). Bimetallic colloids have also been described, in particular for use as catalysts, by Wang et al. (Polymer Bulletin 25 (1991) 139).

It is furthermore known that silver ions in the form of silver salts represent toxicologically acceptable antiseptics with a wide action spectrum. Thus, 1% strength silver nitrate solution is, in Credé's method (prevention of gonoblennorrhea), administered into the conjunctival sac of babies immediately after birth.

It is an object of the present invention to control not only the release of hydrogen peroxide from such complexes but also its decomposition. It is also intended that the complexes have a wide action spectrum.

We have found that this object is achieved by polymer-bound hydrogen peroxide, a metal colloid or metal salt additionally being bound in the polymer.

The present invention therefore relates to polymer complexes which comprise a) hydrogen peroxide, b) a polymer suitable for complex formation with hydrogen peroxide and c) at least one metal colloid and/or metal salt, where components a) and b) form a complex.

The invention furthermore relates to processes for producing these polymer complexes.

$C_1$-$C_n$-alkyl means hereinafter linear, branched or cyclic alkyl groups with 1 to n carbon atoms. Examples are methyl, ethyl, n-propyl, i-propyl, n-butyl, 2-butyl, i-butyl, t-butyl, n-hexyl, 2-hexyl, 2-ethylhexyl or n-decyl, cyclopentyl or cyclohexyl. $C_1$-$C_n$-alkylene means linear or branched alkylene units, for example methylene, ethylene, ethylidene, 1,1-, 1,2-, 1,3-, 2,2-propylene, 1,1-, 1,2-, 1,3-, 1,4-, 2,2-, 2,3-butylene. Aryl groups are phenyl or naphthyl which are unsubstituted or substituted by 1 to 3 $C_1$-$C_4$-alkyl groups or halogen atoms. Component b) is preferably a homo- or copolymer of one or more N-vinyllactams. Preferred N-vinyllactams are N-vinylpyrrolidone, N-vinylpiperidone, N-vinylcaprolactam, N-vinyl-3-morpholinone, N-vinyl-4-oxazolidine and mixtures thereof. Particularly suitable comonomers are N-vinyl heterocycles, eg. vinylpyridines or vinylimidazoles, which may carry one or more $C_1$-$C_4$-alkyl radicals or phenyl radicals. Examples which may be mentioned are: N-vinylimidazole and 2-methyl-1-vinylimidazole, 4-methyl-1-vinylimidazole, 5-methyl-1-vinylimidazole, 2-ethyl-1-vinylimidazole, 2-propyl-1-vinylimidazole, 2-isopropyl-1-vinylimidazole, 2-phenyl-1-vinylimidazole, 2-vinylpyridine, 4-vinylpyridine and 2-methyl-5-vinylpyridine. It is furthermore possible to employ $C_1$-$C_8$-alkyl vinyl ethers, eg. methyl vinyl ether, ethyl vinyl ether, n-propyl vinyl ether, i-propyl vinyl ether, n-butyl vinyl ether, i-butyl vinyl ether, t-butyl vinyl ether, 2-ethylhexyl vinyl ether, vinyl esters of $C_1$-$C_{10}$-alkyl- or $C_6$-$C_{10}$-arylcarboxylic acids, eg. vinyl acetate, vinyl propionate, vinyl butyrate, vinylhexanoate, vinyl 2-ethylhexanoate, vinyl decanoate, vinyl laurate, vinyl stearate or vinyl benzoate. Also suitable are esters of acrylic acid or methacrylic acid with $C_1$-$C_{12}$-alkanols, preferably $C_1$-$C_4$-alkanols. Examples thereof are methyl (meth)acrylate, ethyl (meth)acrylate, n-butyl (meth)acrylate. Further possible comonomers are conjugated $C_4$-$C_8$-dienes such as butadiene or isoprene, vinyl aromatic compounds such as styrene, α-methylstyrene or vinyltoluenes and cationically modified vinyl monomers. Examples of the latter are monoethylenically unsaturated $C_3$-$C_5$-carboxylic esters with amino alcohols of the formula (I)

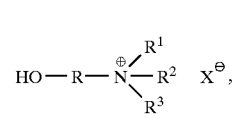

where R is $C_2$-$C_5$-alkylene, $R^1$, $R^2$, $R^3$ are, independently of one another H, $CH_3$, $C_2H_5$, $C_3H_7$ and $X^\ominus$ is an anion. Also suitable are amides of these carboxylic acids derived from amines of the formula

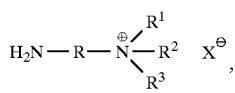

(II)

The substituents in formula II and $X^{\ominus}$ have the meanings as in formula I. Examples of suitable carboxylic acids are acrylic acid, methacrylic acid, crotonic acid, maleic acid (anhydride), fumaric acid and itaconic acid. Suitable cationically modified vinyl monomers are also salts or quaternization products of N-vinylimidazole and 1-vinyl-2-methylimidazole.

The polymers used for the polymer complexes according to the invention contain said N-vinyllactams in amounts of more than 20% by weight, preferably 30 to 99% by weight and, in particular, 35 to 80% by weight, and the comonomers in amounts of up to 80% by weight, preferably 1 to 70% by weight and, in particular, 20 to 65% by weight, the parts by weight being based on the polymer in each case.

These polymers may furthermore contain crosslinking monomers in amounts of up to 20% by weight, preferably up to 5% and in particular, 0.1 to 3% by weight, in each case based on the polymer. Suitable crosslinkers are, as a rule, compounds which have at least 2 nonconjugated ethylenic double bonds in the molecule. Examples thereof are N,N'-methylenebisacrylamide, polyethylene glycol diacrylates and polyethylene glycol dimethacrylates, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, polyhydric alcohols, such as glycerol or pentaerythritol, which are esterified two or three times with acrylic acid or methacrylic acid, triallylamine, tetraallylethylenediamine, trimethylolpropane diallyl ether, pentaerythritol triallyl ether, N,N'-divinylethyleneurea and/or N,N'-divinylpropyleneurea. Also suitable are divinyl aromatic compounds such as divinylbenzene, but also dicyclopentadiene, vinyl (meth) acrylate, vinylnorbornene, tricyclodecenyl (meth)acrylate.

In a preferred embodiment, water-soluble polymers are employed. "Water-soluble" means here that the polymers used according to the invention have a solubility of at least 0.5 g, preferably at least 2 g and, in particular, at least 5 g in 100 g of water at 20° C. Preferred comonomers in this case are vinyl acetate, vinyl propionate, methyl acrylate, ethyl acrylate, n-propyl acrylate, n-butyl acrylate, methyl methacrylate, ethyl methacrylate, acrylonitrile, methacrylonitrile and vinylimidazole. Also suitable are copolymers of the N-vinyllactams with one another. Particularly preferred are copolymers of N-vinylpyrrolidone and N-vinylcaprolactam, N-vinylpyrrolidone and vinyl acetate, and homopolymers of N-vinylpyrrolidone. These water-soluble homo- and copolymers have Fikentscher K values (see Cellulose-Chemie 13 (1932) 48–64 and 71–94) in the range from 10 to 110, preferably 20 to 100.

The preparation of water-soluble polymers based on N-vinyllactams is described, for example, in DE-A 22 18 935 or the earlier application P 196 09 864.5. They are preferably prepared by vent, for example in water, methanol, ethanol, i-propanol or mixtures thereof.

Particularly suitable initiators for the free-radical polymerization are those suitable for free-radical polymerization in aqueous solution. Particularly suitable are aliphatic or cycloaliphatic azo compounds, eg. 2,2'-azobis-(isobutyronitrile), 2,2'-azobis(2-methylbutyronitrile), 2,2'-azobis(2,4-dimethylvaleronitrile), 1,1'-azobis(1-cyclohexanecarbonitrile), (2-carbamoylazo)isobutyronitrile, 4,4,-azobis(4-cyanovaleric acid) and its alkali metal and ammonium salts, dimethyl 2,2'-azobisisobuty-rate, 2,2'-azobis[2-(2-imidazolin-2-yl)propane], 2,2'-azo-bis(2-amidinopropane) and the acid addition salts of the last two compounds mentioned. Also suitable as initiators are hydrogen peroxide, hydroperoxides in combination with suitable reducing agents and peroxo salts. Examples of suitable hydroperoxides are t-butyl hydroperoxide, t-amyl hydroperoxide, cumene hydroperoxide and pinane hydroperoxide, each in combination with, for example, 20 a salt of hydroxymethanesulfinic acid, an iron(II) salt or ascorbic acid. Suitable peroxo salts are, in particular, alkali metal peroxodisulfates. The amount of initiator used is, based on the monomers, in the range from 0.02 to 15 mol%, preferably 0.05 to 3 mol%.

The polymerization is normally carried out at a neutral pH in the range from 5 to 9. If necessary, the pH is adjusted or maintained by adding a base such as ammonia or an acid such as HCl or a buffer system. If low molecular weights are required, the reaction may also be carried out in the presence of a compound which controls the molecular weight of the polymers. Examples thereof are aldehydes such as formaldehyde, acetaldehyde, propionaldehyde or allyl compounds such as allyl alcohol. It is also possible to use regulators which contain sulfur in organically bonded form. Examples thereof are butyl mercaptan, n-hexyl mercaptan, n-dodecyl mercaptan, water-soluble compounds such as bisulfites, disulfites, ethyl thioglycolate, cysteine, 2-mercaptoethanol, mercaptoacetic acid, 3-mercaptopropionic acid, thioglycerol, thiodiglycol, thiourea or dimethyl sulfoxide.

The resulting polymer solutions generally have solids contents in the range from 3 to 70% by weight, preferably 30 to 60% by weight. They can be employed for the processes according to the invention in the form in which they result from the polymerization, without further isolation or treatment, or else be isolated as dry substance by precipitation or removal of the solvent.

In another preferred embodiment, insoluble polymers are employed. Polymers of this type are obtained by polymerizing the monomers in the presence of one of the above-mentioned crosslinkere. However, the polymers can also be crosslinked subsequently by physical effects, such as radiation or by chemical reaction with a bi- or polyfunctional compound able to react with the functional groups present in the polymers, and thus be rendered insoluble. Processes of these types are known to the skilled worker and described in the literature. A particularly preferred embodiment of the insoluble polymers comprises the popcorn polymers (R ömpp, Chemie-Lexikon, 9th Edition, "Popcorn Polymerisate" and literature cited therein). The preparation of popcorn polymers is described, for example, in EP-A 88 964 and EP-A 438 713. As a rule, they are prepared by bulk, solution or precipitation polymerization of the monomers, preferably in the presence of small amounts of a crosslinker (0.1–4% of the weight of the monomers).

The polymer complexes according to the invention contain as metal component c) preferably a metal salt or metal colloid of copper, silver, gold, rhodium, iridium, palladium or platinum. Colloids of copper or silver are particularly preferred, especially of silver. Examples of suitable silver salts are silver nitrate, silver acetate, silver lactate, silver phosphate, silver chloride, silver bromide, silver hydroxide, silver carbonate, silver oxide, silver periodate and the sodium chloride/silver chloride complex ($Na[AgCl_2]$). Silver colloids can be obtained, for example, by treating aqueous solutions of a suitable silver salt with a reducing agent such as hydrogen, ascorbic acid, ribose, glucose, hydrazine, an aldehyde or an alcohol see Römpp, Chemie-Lexikon, 9th Edition "Kolloide"). The complexes according to the invention contain hydrogen peroxide in amounts of, preferably, from 0.5 to 40%, particularly preferably 5 to 23% and, in particular, 6 to 15% of the weight of the finished polymer complex. The polymer content is, as a rule, 55 to 99.5% by weight, preferably 74 to 95% by weight and, in particular, 83 to 94% by weight. The metal content in the polymer complexes is, as a rule, from 0.001 to 5% by weight, preferably 0.005 to 3% by weight and, in particular, 0.01 to 2% by weight.

The polymer complexes according to the invention can be prepared in various ways depending on the nature of the polymers used and the metal component. When soluble polymers are used, spray drying or spray granulation has proven suitable. This entails preferably aqueous solutions of the polymers being spray dried or granulated together with solutions of hydrogen peroxide and with solutions of the metal salts or dispersions of the metal colloids using multicomponent nozzles. It is also possible for the solutions to have been mixed beforehand. Hydrogen peroxide solutions stabilized by metal salts or colloids can also be employed. In another variant, a metal colloid is deposited in the presence of a polymer from an aqueous solution by one of the reducing agents mentioned. The deposition of metal colloids in the presence of vinylpyrrolidone polymers has been reported in the literature, see above. The resulting dispersion is then spray dried together with a hydrogen peroxide solution. It is also possible in this case to mix the solutions beforehand. The polymer solutions can be prepared by dissolving the polymer in a suitable solvent, preferably a hydroalcoholic or aqueous solvent. It is also possible for the solutions resulting from the polymerization to be used directly. In the process according to the invention, hydrogen peroxide is employed in the form of 20 to 70% by weight, preferably 30 to 60% by weight, aqueous solutions.

Processes for spray drying or spray granulation are known to the skilled worker. It is also possible in the present case for the solid polymer complexes to be obtained in spray towers of conventional design. The drying gases used are inert gases such as nitrogen, which are passed countercurrently or, preferably, cocurrently with the drops of liquid through the drying tower. The gas temperature at the tower inlet is, as a rule, from 60 to 180° C., preferably 100 to 160° C., and the temperature at the tower outlet is from 40 to 100° C., preferably 60 to 90° C. The pressure is, as a rule, in the range from 0.6 to 1.5 bar, and the drying preferably takes place under atmospheric pressure. The resulting solid can be removed from the gas stream in a conventional way, for example by a cyclone. This results in a free-flowing powder with a residual solvent content<7.5% of the weight of the finished polymer complex. The particle size in the resulting powder is generally from 10 to 150 μm, and in the case of spray granulation particle sizes up to 450 μm can be obtained.

Another embodiment of the complexes according to the invention comprises reacting the insoluble forms of the N-vinyllactam polymers in a fluidized bed with metal salt solution or metal colloid and hydrogen peroxide. Once again, it is possible for the metal component to be mixed with the hydrogen peroxide solution before-hand.

In another embodiment, the complexes according to the invention have a shell-like structure. This shell-like structure is obtained by applying the abovementioned components or combinations of these components successively to a solid carrier in a suitable apparatus, for example a coating pan or a fluidized bed granulator. These processes are also known to the skilled worker in principle. This solid carrier comprises inorganic oxides such as titanium dioxide, aluminum oxide, silicon dioxide, silicates, aluminosilicates, organic carrier materials such as cellulose, starch, insoluble polymers, preferably those suitable for complex formation with hydrogen peroxide, in particular those based on polyvinyllactams. The last-mentioned carrier can also be used as component b) in the preparation of the complexes according to the invention.

Polymer complexes according to the invention with a layered structure are prepared by spraying solutions or suspensions of components a) and c), with or without b), onto the carrier in the sequence necessary for the required structure in one of the abovementioned apparatuses under the conditions which have been described for the polymer complex powders. This process can be repeated where appropriate until the required relative concentrations of the components are set up. The components can be sprayed on through multicomponent nozzles simultaneously or else successively in any sequence.

If the release of hydrogen peroxide and of the metal is to be dependent on the pH, the complexes can be coated with a polymeric foam former which dissolves or swells at a particular pH. Release can be initiated both in acidic and in alkaline medium by suitable choice of these film formers. In the case of complexes with shell-like structure, film formers of this type may also demarcate the individual layers from one another so that, for example, the active substance is released from a first layer at a neutral pH and from an inner layer only above or below a particular pH. Suitable polymeric film formers are known in pharmaceutical technology. Examples thereof are hydroxypropylcellulose, hydroxypropylmethylcellulose, vinylpyrrolidone/vinyl acetate copolymers, cellulose acetate phthalate, hydroxypropylmethylcellulose phthalate, shellac, copolymers of acrylic acid or methacrylic acid with (meth)acrylic esters, eg. copolymers of ethyl acrylate and methacrylic acid (eg. Kollicoat® MAE 30D or Eudragits®) or copolymers of dimethylaminomethacrylic acid with neutral methacrylic esters.

Preferred embodiments of the shell-like complexes according to the invention have the following structure:

Core: polymer b) with component a); shell: polymer b) with component c);

Core: polymer b) with component a); shell 1: polymeric film former (see above.), shell 2: polymer b) with component c);

Core: polymer b) with component c); shell 1: polymeric film former (see above), shell 2: polymer b) with component a).

Also conceivable are shell-like structures which contain component b) with component a) and/or component c) as core and have a polymeric film former as shell.

In the preparation of the polymer complexes according to the invention, whether as polymer powder or as shell-like granules, further components which simplify the processing of the polymer complexes according to the invention, or extend their action spectrum, may be present. For example, it is possible to add in the preparation of the complexes according to the invention surfactants, which subsequently remain in the complex. These may, on contact with germs, increase the effect of the actual hydrogen peroxide/metal/polymer disinfectant system and serve as solublizers or wetting agents. Suitable surfactants can be cationic, anionic and nonionic in nature. Examples thereof are sodium dodecyl sulfate, dodecyltrimethylammonium bromide, dimethylalkylbenzylammonium chloride, polysorbate fatty acid esters and ethoxylated mono-, di- and trialkylphenols (EO degree: 3 to 50, alkyl radical:$C_4$–$C_9$), ethoxylated fatty alcohols (EO degree: 3 to 50, alkyl radical: $C_8$–$C_{36}$), and alkali metal and ammonium salts of alkyl sulfates (alkyl radical: $C_8$–$C_{12}$), of sulfuric monoesters of ethoxylated alkanols (EO degree: 4 to 30, alkyl radical: $C_{12}$–$C_{18}$) and ethoxylated alkylphenols (EO degree: 3 to 50, alkyl radical: $C_4$–$C_9$), of alkylsulfonic acids (alkyl radical: $C_{12}$–$C_{18}$) and of alkylarylsulfonic acids (alkyl radical: $C_9$–$C_{18}$). Preferred emulsifiers are sodium dodecyl sulfate and polysorbate fatty acid esters.

Examples of suitable substances for increasing the action spectrum of the polymer complexes according to the invention are aldehydes and α-hydroxy carboxylic acids. Examples of aldehydes are glutaraldehyde and glyoxal. The α-hydroxy carboxylic acids which are preferably chosen are those pharmaceutically suitable for topical administration. Examples thereof are glycolic acid, lactic acid, hydroxyoctanoic acid, malic acid, pyruvic acid and citric acid. Also suitable are hydroxyarylcarboxylic acids, for example salicylic acid, 3-hydroxybenzoic acid, 4-hydroxybenzoic acid, 2,4-dihydroxybenzoic acid, 3,4-dihydroxybenzoic acid and 3,5-dihydroxybenzoic acid. Said compounds are presumably likewise bound in a complex with the polymer (see D. Horn et al., J.Pharm.Sci., 71 (1982) 1021–1026).

The complexes according to the invention are solids at room temperature and thus are stable for a long period without loss of hydrogen peroxide. The combination of hydrogen peroxide, polymeric carrier and stabilizing metals salt or colloid in the use forms according to the invention results in slow release of the hydrogen peroxide and controlled disintegration. In respect of the disinfectant action of the complexes according to the invention, they have the advantage over halogenated disinfectants, eg. the well-known iodine/polyvinylpyrrolidone complexes, that they are colorless and tasteless. The halogen complexes may moreover irritate the skin. Compared with the pure polymer/hydrogen peroxide complexes, their action spectrum is increased because metal colloids and their ions also have wide-ranging bactericidal properties.

The bactericidal effect of the complexes according to the invention in particular permits a large number of applications. Since the complexes according to the invention contain as a rule starting materials which are pharmaceutically accepted, and since they are inert toward most ingredients used in pharmaceutical formulations, there are scarcely any restrictions on their formulation in pharmaceutical compositions. The ingredients used in the formulations are the usual pharmaceutical or cosmetic carriers and auxiliaries appropriate for the required formulation. Examples of formulation ingredients which can be used are alcohols such as ethanol, propanol, isopropanol, phenoxyenthanol 1-phenoxy- and 2-phenoxypropanol, polyols such as Propylene glycol, glycerol or polyethylene glycols, silicones, esters or glycerides of fatty acids, for example isopropyl myristate, myricyl cerotate, cetyl palmitate, glycerides of palmitic acid, stearic acid, linoleic acid, linolenic acid or oleic acid, phospholipids, such as cephalins or lecithins, starches, modified starches or hydrocarbons, for example petrolatum or paraffins. The formulations may furthermore contain ingredients which themselves have pharmaceutical activity, such as the aldehydes mentioned and the a-hydroxy carboxylic acids mentioned, or agents necessary for their production, eg. the surfactants mentioned.

The compositions according to the invention are primarily administered topically. The complexes according to the invention can be formulated in dusting powders, ointments, creams or gels for wound management in human or veterinary medicine or for managing bacterial infections of skin, for example acne vulgaris. The complexes according to the invention are furthermore suitable for formulations as mouthwashes, toothpastes or tooth powders. Other topical formulations are antibacterial lip salves, ear drops and vaginal suppositories. The complexes according to the invention can also be formulated in solutions for irrigating body cavities for the treatment of fistulas. When soluble complexes are used, they can be converted into films together with adhesives for plasters. The plasters produced in this way have a depot disinfectant effect. Because the polymer complexes according to the invention have a combination of disinfectant and deodorant effects, they are also suitable for formulation as body care compositions. Since the complexes according to the invention are in the form of solids, there are no difficulties in formulating them for medical applications in a conventional way. There are in principle no restrictions on the formulation ingredients except compatibility with the complexes according to the invention.

The complexes according to the invention can be formulated in cosmetics as a cream, ointment or gel, for example in cosmetics for dyeing or bleaching hair, and for depilation. Use in shampoos, eg. for treating dandruff, in soaps or powder sprays is also conceivable.

Another application of the complexes according to the invention is in the sterilization of liquids. Thus, the water-insoluble embodiments of the complexes according to the invention are suitable as filter inserts for sterilizing drinking water or beverages. Use in filter systems for swimming baths is likewise conceivable.

A third application of the complexes according to the invention is in the bactericidal finishing of articles. Since the solubility properties of the polymer complexes can be tailored by suitable choice of the comonomers, the polymer complexes according to the invention can be incorporated into a wide variety of materials, for example into coating compositions, impregnation solutions or adhesive dispersions. It is thus possible to provide both smooth surfaces and woven or nonwoven fabrics or random fiber webs, or else pressed pulp materials, with a bactericidal finish. Examples thereof are the lining of liquid tanks, eg. in drinking water systems or tanks for excreta in chemical toilets. It is likewise possible to provide sponges, towels, garments, bed linen, net and other curtains with a bactericidal finish using the complexes according to the invention. A conceivable application in the medical sector is the finishing of surgical gloves, face masks, tampons, pads or swabs with the complexes according to the invention. Finishing of inserts, especially for adult incontinence or for period hygiene, diapers, sport shoes, bathmats, head or neck supports, is possible.

The complexes according to the invention are furthermore suitable for use in filters for air conditioning systems. Combinations of the complexes according to the invention with adsorbents and desiccants can be used in pet hygiene, for example as bedding or material for laying in cages.

The complexes according to the invention can also be used as ingredients in cleaners and/or disinfectants. Examples thereof are, on the one hand, household cleaners or disinfectants, especially for medical practices and for hospitals, but also, on the other hand, cleaning compositions or tablets for denture cleaning or cleaning dental braces or solutions for disinfecting contact lenses.

One industrial application of the complexes according to the invention is their effect as free-radical initiators, for example for polymerizing olefinically unsaturated polymers.

The following examples are intended to illustrate the invention without, however, restricting it.

EXAMPLES

Preparation of the Polymer/Hydrogen Peroxide Complexes

EXAMPLES 1 to 5

Components Used

Hydrogen peroxide: 50% strength aqueous solution stabilized with 0.082% by weight of colloidal silver; commercial product from Hungerbach GmbH, Morsdorf.

Polyvinylpyrrolidone K30: K value 30 by the method of H. Fikentscher, Cellulose-Chemie 13 (1932) 48, 71; commercial product from BASF.

Polyvinylpyrrolidone, crosslinked: Crospovidone®, commercial product from BASF AG.

Polyvinylcaprolactam: K value 30

Vinylimidazole/vinylpyrrolidone copolymer (VI/VP=9:1) prepared by the following method:

A mixture of 9 parts of N-vinylimidazole (VI), 1 part of N-vinylpyrrolidone (VP), 0.3 part of N,N'-divinylimidazolidone, 100 parts of water and 0.1 part of sodium hydroxide solution (5% strength) was introduced into an apparatus with stirrer and reflux condenser and, with addition of 0.1 part of a crosslinked polymer of low swellability based on VI and/or VP, heated to 70° C. in a stream of nitrogen. Polymerization was carried out at this temperature for 6 h. The precipitated polymer was filtered off with suction, thoroughly washed with water and dried at 60° C. A white granular product was obtained in a yield of 96.5%.

Ethylacrylate/methacrylic acid copolymer (EA/MAA: 1/1): Kollicoat MAE30 D from BASF AG.

Analyses

The hydrogen peroxide content in the polymer complexes according to the invention was determined by titration against potassium permanganate.

The metal content in the polymer complexes according to the invention was determined by atomic absorption spectrometry. The water content in the polymer complexes was determined by Karl-Fischer titration.

Homogeneous Polymer/Hydrogen Peroxide/Silver Complexes

Examples 1–3

Example 1 (Preparation by spray drying)

A Solution of 500 g of polyvinylpyrrolidone K30

153 g of hydrogen peroxide (50% strength aqueous solution stabilized with 0.126 g of colloidal silver) and 1347 g of water was sprayed with a two-component nozzle in a drying tower (D 900 mm; H 1400 mm) under a pressure of 1.5 bar. Drying took place using nitrogen under 1 bar with a tower inlet temperature of 160° C. and a tower outlet temperature of 70° C. The resulting powder was removed from the gas stream in a cyclone. The resulting powder had a peroxide content of 12.9% by weight, a silver content of 0.019% by weight and a water content of 3% by weight.

Example 2 (Preparation by spray drying)

150 g of polyvinylpyrrolidone and 5.6 g of silver nitrate were dissolved in 500 ml of ethanol and refluxed for 60 min. Subsequently, 60 g of a 25% strength aqueous hydrogen peroxide solution were added. The resulting solution was spray dried as in Example 1. The resulting powder had a peroxide content of 8% by weight, a silver content of 1.9% by weight and a solvent content of 1% by weight.

Example 3 (Preparation by fluidized bed drying)

Preparation by fluidized bed drying takes place in a granulating cylinder which is closed at the bottom by a perforated plate, on which a screen (mesh width 10–500 $\mu$m) is placed and at the top by 4 filter bags which are blown free by compressed air every 15 sec. 28 cm above the screen plate there is a two-component nozzle oppositely directed to the screen plate. The hydrogen peroxide/silver solution is metered by a peristaltic pump with addition rates of 2.5 to 100 g/min/1000 g of polymer. The amount of polymer used is from 100 to 4000 g. The gas throughput is controlled by an outlet air valve and is 120 $m^3$/h to 150 $m^3$/h. Nitrogen is used as process gas. The inlet air temperature is in the range from 25 to 80° C., and the outlet air temperature is in the range from 25 to 70° C.

250 g of polyvinylcaprolactam were introduced into the fluidized bed with the gas stream at 120 $m^3$/h and, at 50° C. 153 g of a 50% by weight aqueous hydrogen peroxide solution which contained 0.126 g of colloidal silver were sprayed on at (10 g/min). Drying was then carried out in the gas stream at 50° C. (150 $m^3$/h; 20 min). The peroxide content of the resulting powder was 23% by weight, the silver content was 0.035% by weight and the water content was 1% by weight.

Shell-like Polymer/Hydrogen Peroxide/Silver Complexes Examples 4 to 7

Example 4 (VI/VP/hydrogen peroxide/silver complex)

200 g of insoluble VI/VP polymer were introduced into a fluidized bed granulator as in Example 3 and, at 60° C., sprayed with 20% strength hydrogen peroxide solution in 25 ml portions in 4 periods and then with 50 ml portions in 3 periods (20 ml min in each case). Drying was carried out in the gas stream for 5 min between each of the spraying periods. 250 ml of an aqueous silver colloid suspension with a silver content of 0.16% by weight was sprayed on to the resulting polymer/hydrogen peroxide complex in the same way. The resulting complex had a peroxide content of 16.8% by weight, a silver content of 0.196% by weight and a water content of 3.7% by weight.

Example 5 (Polymer/hydrogen peroxide/silver complex with film former)

100 g of crosslinked polyvinylpyrrolidone was initially sprayed with 200 ml of a 15% strength hydrogen peroxide solution as in Example 4. The resulting polymer/hydrogen peroxide complexes were sprayed in 4 portions with a solution of 15 g of Kollicoat MAE 30 D, 2 g of triethyl citrate and 0.1 g of colloidal silver in 100 ml water and dried as in Example 3. The resulting complex had a peroxide content of 18% by weight, a silver content of 0.06% by weight and a water content of 2% by weight. Silver and hydrogen peroxide were released at pH 5.5.

Example 6

100 g of crosslinked polyvinylpyrrolidone were initially sprayed with 200 ml of a 15% strength hydrogen peroxide solution as in Example 4. The resulting polymer/hydrogen peroxide complexes were sprayed in 4 portions with a solution of 15 g of Kollicoat MAE 30 D and 2 g of triethyl citrate. Subsequently a solution of 0.1 g of colloidal silver in 100 ml of water was sprayed on, and drying was carried out as in Example 3.

Example 7

The procedure was as in Example 6 but a 0.1% by weight solution of silver nitrate was used in place of the silver colloid. The silver content in the resulting complex was 0.04% by weight.

Formulations of the polymer complexes according to the invention

Examples 8 to 12

Components used

Polyacrylic acid: Carbopol® C981, from BF Goodrich Chemical

Ethylene oxide/propylene oxide block copolymer (EO/PO 70/30) $M_n$ 9840 to 146000; Lutrol® F 127 from BASF.

Polyethylene glycol: $M_n$ 400; Lutrol® E 400 from BASF.

Polyethylene glycol: $M_n$ 4000; Lutrol® E 4000 from BASF.

Silcone oil: density @(25° C.) 0.95 g/Cm$^3$, Viscosity (25° C.) 2.5 mm$^2$/s, Dow Corning Fluid 344 (cyclic tetra (dimethyl)siloxane from Dow-Corning).

Distarch phosphate based on corn starch: maize PO4 100 K (P content:<0.1% by weight in dry matter); supplied by Hauser KG Example 8 (Formulation as tooth cream)

10 g of the complex prepared in Example 1 were dissolved in 78 g of water and processed with 2 g of Carbopol® and 10 g of 1,2-propylene glycol in a vacuum homogenizer to give a gel free of air bubbles.

Example 9 (Gel for disinfection of skin)

10 g of complex from Example 1, 75 g of water, 5 g of 1,2-propylene glycol and 20 g of Lutrol® F127 were processed to give a gel at below 10° C. in the manner described for Example 6.

Example 10 (Formulation as ointment)

20 g of complex from Example 1 were dissolved in a mixture of 50 g of Lutrol® E 400 and 5 g of water and heated to 55–60° C. Subsequently, at this temperature, 25 g of Lutrol® E 4000 were incorporated with stirring, and the mixture was left to cool with stirring.

Example 11 (Formulation as concentrate for mouth washes)

25 g of complex from Example 1 were dissolved in a mixture of 1 g of 1,2-propylene glycol, 9 g of ethanol and 65 g of water.

Example 12 (formulation as powder spray)

2.5 g of complex from example 1 were micronized and transferred together with 1 g of silicone oil (see above) and 2.5 g of corn starch diphosphate into a pressure vessel. 5 g of pentane and 2.2 g of propane/butane were then introduced.

We claim:

1. A solid, pulverulent or granular polymer complex, comprising as essential components a) hydrogen peroxide, b) at least one polymer suitable for complex formation with hydrogen peroxide and c) at least one metal colloid or metal salt, wherein the metal is selected from the group consisting of Cu, Ag, Au, Rh, Ir, Pd and Pt.

2. The polymer complex defined in claim 1, wherein component b) is a polymer based on a N-vinyllactam.

3. The polymer complex defined in claim 2, wherein the N-vinyllactam is selected from the group consisting of N-vinylpyrrolidone, N-vinylpiperidone, N-vinylcaprolactam, N-vinyl-3-morpholinone and N-vinyl-4-oxazolidinone.

4. The polymer complex defined in claim 1, wherein component b) is composed of

20–100% by weight of at least one N-vinyllactam,

0–80% by weight of at least one copolymerizable, monoethylenically unsaturated monomer and 0–20% by weight of at least one crosslinking monomer.

5. The polymer complex defined in claim 1, wherein the polymeric component b) is a homo- or copolymer of N-vinylpyrrolidone or N-vinylcaprolactam with a K value of from 10 to 110.

6. The polymer complex defined in claim 1, wherein component C) is a silver colloid or silver salt.

7. The polymer complex defined in claim 1, with a shell-like structure, in which a plurality of complexes is arranged on a core.

8. The polymer complex defined in claim 7, wherein the core is a cross-linked, water-insoluble polymer suitable for complex formation with hydrogen peroxide.

9. The polymer complex defined in claim 7, with a multi-shell structure, where the core consists of polymer b) with components a) and/or c) and the shells consist of polymer b) with components a) and/or c) or of a polymeric film former.

10. The polymer complex defined in claim 1, comprising component a) in an amount of from 0.5 to 40% by weight, component b) in an amount of from 55 to 99.5% by weight, component c) in an amount of from 0.001 to 5% by weight, in each case based on the total weight of the polymer complex.

11. A process for preparing a polymer complex as claimed in claim 1, which comprises components a), b) and c) being brought into contact with one another or, where appropriate, being applied to a core.

12. A bactericidal composition in the form of a cosmetic or pharmaceutical composition or in the form of a composition for disinfecting aqueous liquids and articles, said composition containing an effective amount of a polymer complex as defined in claim 1.

* * * * *